United States Patent

Bauer et al.

Patent Number: 5,449,816
Date of Patent: Sep. 12, 1995

[54] AMINO-OXY ESTERS

[75] Inventors: Gerhard Bauer, Weinheim; Kaspar Bott, Mannheim, both of Germany

[73] Assignee: BASF Aktiengesellschaft, Ludwigshafen, Germany

[21] Appl. No.: 319,637

[22] Filed: Oct. 7, 1994

[30] Foreign Application Priority Data

Oct. 19, 1993 [DE] Germany .............. 43 35 555.2

[51] Int. Cl.$^6$ .................. C07C 271/00; C07C 69/533
[52] U.S. Cl. .................................. 560/157; 560/205
[58] Field of Search ............................ 560/157, 205

[56] References Cited

U.S. PATENT DOCUMENTS

| | | |
|---|---|---|
| 4,250,070 | 2/1981 | Ley et al. . |
| 4,396,738 | 8/1983 | Powell et al. . |
| 4,433,095 | 2/1984 | Hombach et al. . |
| 4,452,963 | 6/1984 | Moriarity ............................ 528/49 |
| 4,663,377 | 5/1987 | Hombach et al. . |

FOREIGN PATENT DOCUMENTS

| | | |
|---|---|---|
| 2069674 | 11/1992 | Canada . |
| 3516 | 8/1979 | European Pat. Off. . |
| 516074 | 12/1992 | European Pat. Off. . |
| 522306 | 1/1993 | European Pat. Off. . |
| 617013 | 9/1994 | European Pat. Off. . |
| 3112117 | 10/1982 | Germany . |
| 3521618 | 12/1986 | Germany . |
| 3807555 | 9/1988 | Germany . |
| 4219385 | 12/1993 | Germany . |
| 419169 | 2/1967 | Switzerland . |
| 93/25519 | 12/1993 | WIPO . |
| 93/25588 | 12/1993 | WIPO . |

*Primary Examiner*—Joseph L. Schofer
*Assistant Examiner*—Wu C. Cheng
*Attorney, Agent, or Firm*—Keil & Weinkauf

[57] ABSTRACT

The invention relates to hydroxylamine derivatives of the general formula

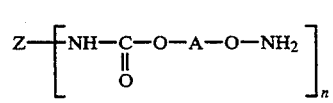

or

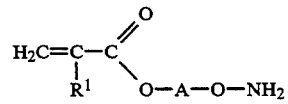

in which A denotes a divalent connecting link, $R^1$ can be a hydrogen atom or a $C_1$–$C_4$alkyl group, Z stands for an n-valent organic radical, which contains a copolymerizable ethylenically unsaturated group, and n is an integer from 1 to 3, and salts thereof and copolymers thereof.

1 Claim, No Drawings

AMINO-OXY ESTERS

The invention relates to hydroxylamine derivatives of the general formula $$Z \text{---} \left[ \text{NH} \text{---} \underset{\underset{O}{\|}}{C} \text{---} O \text{---} A \text{---} O \text{---} NH_2 \right]_n \qquad I$$

or $$H_2C = \underset{R^1}{\overset{|}{C}} \text{---} C \overset{\displaystyle\nearrow O}{\underset{\displaystyle\searrow O \text{---} A \text{---} O \text{---} NH_2}{}} \qquad II$$

in which A denotes a divalent connecting link, $R^1$ can be a hydrogen atom or a $C_1C_4$alkyl group, Z stands for an n-valent organic radical, which contains a copolymerizable ethylenically unsaturated group, and n is an integer from 1 to 3, and their salts.

Furthermore, the invention relates to a process for the preparation of the hydroxylamine derivatives and their salts, and to copolymers, containing the hydroxylamine derivatives.

Copolymers used in coating formulations or adhesives, are frequently cross-linkable copolymers. Cross-linking can result in, e.g., protective coatings or coatings of adhesive having good elastic properties, high cohesion, high resistance to chemicals and solvents.

In order to effect cross-linking, a cross-linking agent is generally added to the copolymers, which reacts with functional groups in the copolymer. Possible cross-linking agents are, e.g., polyisocyanates, which react with hydroxyl groups or amino groups.

DE-A 3,521,618 describes corresponding aqueous adhesive preparations, in which polyisocyanates dispersed in water are added to aqueous dispersions of free-radically polymerized copolymers to act as cross-linking agents. Similar adhesive preparations are also described in U.S. Pat. No. 4,396,738 and DE-A 3,112,117.

A drawback of these aqueous preparations is, however, their poor storage stability. The polyisocyanate may therefore be dispersed in water and mixed with the copolymer only just before its use as a cross-linking agent.

An increase in the storage stability can be achieved by reaction of the isocyanate groups with blocking agents, e.g., oximes, caprolactam, phenols, dialkyl maleates. The 'blocked' polyisocyanates obtained hydrolyze in aqueous dispersion only to a minor extent.

The subject of DE-A 3,807,555 is such a diisocyanate blocked with oximes, which is dispersed in water and is suitable for addition to polymers dispersed in water.

In the systems described in this specification, however, cross-linking reactions do not occur until elimination of the blocking agent takes place at temperatures above ca 130° C.

Aqueous adhesive preparations known in the art which include polyisocyanates as cross-linking agents are, therefore, either not stable in storage and therefore only usable as a dual-component system or they cross-link only at high temperatures.

Storage-proof aqueous dispersions which cross-link at room temperature on removal of the solvent are disclosed in EP-A 35 16 known. These dispersions contain polyhydrazides, which react with monomers containing carbonyl groups and contained in the copolymer in the form of polymerized units.

Furthermore, EP-A 516,074 discloses dispersions containing aminoxy cross-linking agents. German Patent Applications P 41 21 946.5 (= EP-A 522,306) and P 42 19 385.0 and P 43 09 193.8 respectively describe polyisocyanates blocked with oxime and copolymerizable oxime ethers acting as cross-linking agents. In each case, cross-linking occurs with copolymers containing carbonyl groups. German Patent Application P 43 14 623.6 describes non-copolymerizable hydroxylamines.

It is a basic desire to make available other dispersions which are stable in storage and which cross-link at room temperature, in order to provide alternatives to the polyhydrazide cross-linking systems. In particular, it is also desirable to have cross-linking monomers which can be copolymerized and thus rendered incapable of escaping from, e.g., coating compositions.

The present invention therefore relates to cross-linkable copolymers which are stable when stored in dispersion or solution even in the presence of a cross-linking agent and can be cross-linked at room temperature.

Accordingly, we have found the hydroxylamine derivatives defined above and the salts thereof and a process for the preparation thereof.

Furthermore, copolymers have been found which contain polymerized units of the aforementioned hydroxylamine derivatives in uncombined form or in the form of salts and a method of using the copolymers as coating compositions or adhesives.

The copolymers containing the hydroxylamine derivatives demonstrate good adhesion (wet or dry) to a large variety of substrates and cross-link particularly well with compounds containing aldehyde oder keto groups.

The variable A in the formulas I and II is preferably a linear or branched hydrocarbon chain having from 2 to 12, in particular from 2 to 8, carbon atoms, which can be optionally interrupted by 1 to 3, in particular 1 or 2, non-adjacent sulfur or nitrogen atoms or, preferably, oxygen atoms or a $C_5$-$C_{10}$-Cycloalkylene or a $C_5$-$C_{10}$arylene ring. Very preferably, A is a linear or branched hydrocarbon chain having from 2 to 8 carbon atoms.

$R^1$ preferably stands for a hydrogen atom or a methyl group, n stands for an integer from 1 to 3 and is preferably 1.

Z stands for an organic radical, which usually contains a copolymerizable ethylenically unsaturated group.

Z can be a monomer known per se for free-radical polymerization, which, as shown in formula I, is substituted by a group of the formula $$\text{---} \text{NH} \text{---} \underset{\underset{O}{\|}}{C} \text{---} O \text{---} A \text{---} O \text{---} NH_2.$$

Suitable values of Z are, e.g., vinyl-aromatic radicals having up to 20 C-atoms, (meth)acrylic acid radicals of the formula $$H_2C = \underset{R^1}{\overset{|}{C}} \text{---} C \overset{\displaystyle\nearrow O}{\underset{\displaystyle\searrow O \text{---} X \text{---}}{}} \qquad V$$

in which R¹ has the aforementioned meaning and X stands for an organic connecting link usually having from 1 to 20 C-atoms. X preferably stands for a C₁–C₁₀alkylene group such as —CH₂—CH₂—.

Other suitable values of Z include an ethylenically unsaturated monovalent or polyvalent radical containing a urethane group produced from a mono- or poly-isocyanate by abstraction of one or more isocyanate groups. The urethane group in the radical Z can usually be obtained by the reaction of a monomer containing an OH group which is reactive to isocyanates, with a further isocyanate group in Z.

Very preferably, Z is an acroyl group or methacroyl group of the formula

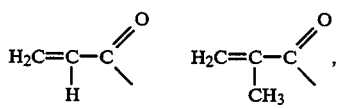

The hydroxylamine derivatives of the formulas I and II or their salts can be obtained starting from oxime ethers of the formulas

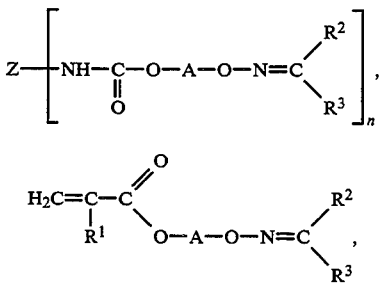

in which A, Z, n, and R¹ have the aforementioned meanings and R² and R³ independently stand for a C₁–C₁₀alkyl, a C₁–C₁₀alkoxy, a C₃–C₁₀cycloalkyl, or a C₅–C₁₀aryl radical, which can also contain one to three non-adjacent nitrogen, oxygen, or sulfur atoms as hetero atoms in the carbon chain or in the carbon ring and can be substituted by one to three C₁–C₄ alkyl or C₁–C₄alkoxy groups, R² or R³ can stand for a hydrogen atom or R² and R³ can together form a bridging member having from 3 to 14 carbon atoms, where some of the carbon atoms can also be part of an aromatic ring.

R² and R³ preferably independently stand for a hydrogen atom, a C₁–C₆alkyl group, a C₁–C₆alkoxy group, or a C₅–C₁₀aryl radical, in particular a phenyl ring. In the case of a hydrogen atom only one of the two radicals R² and R³ can be a hydrogen atom. Xnx stands for an integer from 1 to 3 and is preferably 1. It is particularly preferred that R² be a C₁–C₆ alkyl group, in particular a C₁–C₂alkyl group and R³ a C₁–C₆alkoxy group, in particular a C₁–C₂alkoxy group.

The oxime ethers of formula III or IV are caused to react with a strong acid having an acid constant of more than 10⁻², preferably 10⁻¹ (cf Anorganikum, Berlin, 1977, p. 458), in the presence of water, to produce the hydroxylamine derivatives.

The hydroxylamine derivatives I and II are in this case produced in the form of their salts.

In order to carry out this reaction, the oxime ethers are allowed to react with a mixture of generally water and the corresponding acid usually at from 0° to 50° C. and preferably from 20° to 30° C. In each case from 1 to 4, preferably from 1.5 to 2, equivalents of acid are used per mole of oxime ether III or IV. Examples of suitable acids are perchloric acid, sulfuric acid, aromatic or aliphatic sulfonic acids, phosphoric acid, trifluoroacetic acid, and hydrohalic acids such as HCl or HBr. HCl is preferred.

Good results are achieved when the reaction is carried out in a solvent such as dioxane, methanol, ethanol, n-propanol, isopropanol, and mixtures thereof and the resulting salts are precipitated by a precipitant such as diethyl ether, chloroethane, and toluene.

If desired, the free compounds of the formulas I and II can be obtained in known manner from the salts by carrying out suitable measures to effect deprotonization such as the addition of a base such as K₂CO₃, Na₂CO₃, NaOH, or an aliphatic amine. Salts or adducts of acids other than those mentioned above can be produced in the usual manner by reaction of the free compounds with the corresponding acids. Examples thereof are carbonic acid, acetic acid, propionic acid, bezoic acid and, in particular, formic acid.

The oxime ether compounds of the formula III can be prepared as described in German Patent Application P 43 09 193.8.

The preparation of the copolymerizable oxime ethers of the formula III can be effected by causing oxime ether alkohols of the formula

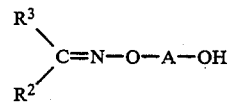

to react with an isocyanate compound of the formula

The reaction can be effected in a simple manner at preferably from 0° to 50° C. and in particular from 0° to 20° C. by mixing the starting compounds, preferably in a stoichiometric ratio of the oxime ether alkohols to the isocyanate groups. The reaction is preferably carried out in the presence of a solvent. Examples of suitable solvents are aromatic or aliphatic hydrocarbons as well as chlorinated hydrocarbons.

The oxime ether alkohols of the formula VII used as starting compounds for the reaction can be obtained by known methods, e.g., by the reaction of oximes with alkylene oxides such as ethylene oxide, propylene oxide etc or with haloalcohols in the presence of a base.

The isocyanate compounds VIII are usually monomers capable of undergoing free-radical polymerization, ie compounds having a copolymerizable ethylenically unsaturated group and containing at least one isocyanate group.

Suitable isocyanate compounds are, e.g., C₁–C₁₀alkyl (meth)acrylates which are substituted in the alkyl radical by at least one, preferably one isocyanate group, e.g., 2-isocyanatoethyl(meth)acrylate and in particular acryloyl isocyanate and methacryloyl isocyanate.

Further isocyanate compounds VIII can be prepared in a simple manner, by causing polyisocyanates, in particular diisocyanates, to react with ethylenically unsaturated compounds, so that at least one free isocyanate group remains. Suitable ethylenically unsaturated compounds are those having at least one group which is reactive to isocyanate, e.g., a primary or secondary amino group or preferably a hydroxyl group, for example, 2-hydroxyethyl(meth)acrylate or p-aminostyrene. These can then be caused to react in known manner with a polyisoCyanate with the formation of urea or urethane. Preferably ethylenically unsaturated compounds having one hydroxy group, e.g., hydroxy-$C_2$–$C_{10}$-alkyl (meth)acrylates, are caused to react with polyisocyanates, in particular diisocyanates. Suitable diisocyanates are, e.g., those having the general formula $X(NCO)_2$, where X stands for an aliphatic hydrocarbon radical having from 4 to 12 C-atoms, a cycloaliphatic hydrocarbon radical having from 6 to 15 atoms or an aromatic or alkaromatic hydrocarbon radical having from 6 to 15 C-atoms. Examples are 1,4-butane diisocyanate, 1,6-hexane diisocyanate, 2,2,4- and 2,4,4-trimethylhexamethylene diisocyanates, cyclohexane diisocyanate, methylcyclohexane diisocyanate, isophorone diisocyanate, 4,4'-diisocyanatodiphenylmethane, 4,4'-diisocyanatodicyclohexylmethane, and 2,4- and 2,6-toluene diisocyanates.

The oxime ether compounds of the formula IV can be prepared as described in German Patent application P 42 19 385.0.

They can be prepared, e.g., by transesterification of oxime ether alkohols of the formula VII with alkyl (meth)acrylates, in particular with methyl (meth)acrylate or ethyl(meth)acrylate.

It is advantageously, however, to cause reaction of oxime ether alkohols with (meth)acrylic chlorides or (meth)acrylic anhydrides of the formula

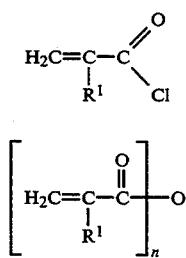

since the reaction times are short and the temperatures of reaction can be kept low so that undesirable side-reactions such as polymerization and decomposition are substantially avoided.

The reaction of the oxime ether alkohols VII with (meth)acrylic chlorides IX preferably takes place with cooling of the reaction mixture at temperatures between 0° and 50° C., in particular at from 10° to 30° C. In the case of the (meth)acrylic anhydrides X the temperature should be above 60° C. The reaction can take place in an organic solvent or alternatively in the absence of solvent. Suitable solvents are, e.g., cyclohexane, methylene chloride, diethyl ether, methyl-tert-butyl ether, and ethylene chloride.

Particularly suitable solvents, also with regard to subsequent purification, are ethers, e.g., diethyl ether. The reaction is preferably carried out in the presence of bases or base-reacting compounds acting as acid binders. Suitable bases or base-reacting compounds are, e.g., tertiary nitrogen compounds such as triethylamine. The base or base-reacting compound is preferably used in an equimolar amount based on the oxime ether alkohol.

On completion of the reaction the reaction mixture can be washed with, e.g., an aqueous sodium carbonate solution and the oxime ether obtained can be purified by distillation optionally following removal of the solvent.

The hydroxylamine derivatives or their salts (also referred to below as monomers a)) can be copolymerized with ethylenically unsaturated monomers by usual free-radical polymerization techniques.

To achieve adequate cross-linkability and good adhesion properties of the copolymers obtained their content of monomers a) contained as polymerized units should be at least 0.01 wt %. A concentration above 30 wt % is generally not necessary.

The content of monomers a) contained as polymerized units in the copolymer is preferably from 0.1 to 10 and more preferably from 0.1 to 5 wt %.

The proportion of main monomer b) in the copolymer is general from 30 to 99.99 wt %, preferably from 70 to 99.9 wt % and more preferably from 85 to 99.9 wt %. The main monomer b) is generally selected from $C_1$–$C_{20}$alkyl (meth)-acrylates, vinyl esters of carboxylic acids containing up to 20 C-atoms, vinyl aromatics containing up to 20 C-atoms, ethylenically unsaturated nitriles, vinyl halides and non-aromatic hydrocarbons having at least 2 conjugated double bonds.

Examples of suitable main monomers are alkyl (meth)acrylates containing a $C_1$–$C_{10}$alkyl radical, such as methyl methacrylate, methyl acrylate, n-butyl acrylate, ethyl acrylate, and 2-ethylhexyl acrylate.

In particular, mixtures of alkyl (meth)acrylates are also suitable.

Vinyl esters of carboxylic acids having from 1 to 20 C-atoms are, e.g., vinyl laurate, vinyl stearate, vinyl propionate, and vinyl acetate.

Suitable vinyl-aromatic compounds are vinyl toluene, α- and p-methylstyrenes, α-butylstyrene, 4-n-butylstyrene, 4-n-decylstyrene, and preferably styrene. Examples of nitriles are acrylonitrile and methacrylonitrile.

The vinyl halides are ethylenically unsaturated compounds substituted with chlorine, fluorine, and bromine, preferably vinyl chloride and vinylidene chloride.

Examples of non-aromatic hydrocarbons having from 2 to 8 C-atoms and at least two olefinic double bonds are butadiene, isoprene, and chloroprene.

Alternatively and preferably, mixtures of the main monomers are used.

Furthermore, the copolymers can also contain monomers having at least one aldehyde oder keto group (monomers c)).

Preferably the monomers have one or two aldehyde or keto groups or one aldehyde and one keto group and one olefinic double bond capable of undergoing free-radical polymerization.

Suitable monomers are, e.g., acrolein, methacrolein, vinyl alkyl ketones having from 1 to 20 and preferably from 1 to 10 carbon atoms in the alkyl radical, formylstyrene, alkyl (meth)acrylates having one or two keto or aldehyde groups, or one aldehyde group and one keto group in the alkyl radical, the alkyl radical preferably containing, in all, from 3 to 10 carbon atoms, e.g., (meth)acroyloxyalkyl propanals as described in D-A 2,722,097. Furthermore, n-oxoalkyl (meth)acrylamides as revealed in, e.g., U.S. Pat. No. 4,226,007, D-A 2,061,213, or D-A 2,207,209 are also suitable.

Particularly preferred compounds are acetoacetyl (meth)acrylate, acetoacetoxyethyl (meth)acrylate, and, in particular, diacetone acrylamide.

The content of said monomers is generally between 0 and 30 wt %, preferably between 0 and 10 and more preferably between 0 ,and 5 wt %.

The copolymer can be cross-linkable with or without assistance. When it is self-cross-linkable it contains both copolymerizable oxime ethers and, preferably, monomers having at least one keto or aldehyde group. Cross-linking of the copolymer then occurs without any addition of cross-linking agent by reaction of the oxime group with the keto or aldehyde group in the same copolymer.

The content of the monomer containing at least one keto or aldehyde group c) in the copolymer should then preferably be at least 0.1 wt %. The maximum possible amount of the main monomer then drops by 0.1 wt %. Monomers c) need not be present to achieve good adhesion properties.

Further monomers d) which differ from the monomers a) to c) and can also be present in the copolymer, are, e.g., esters of acrylic and methacrylic acids with alcohols having from 1 to 20 C-atoms, which contain, in addition to the oxygen atom in the alcohol group at least one further hetero-atom and/or which contain one aliphatic or aromatic ring, such as 2-ethoxyethyl acrylate, 2-butoxyethyl(meth)acrylate, dimethylaminoethyl (meth)acrylate, diethylaminoethyl (meth)acrylate, aryl, alkaryl, or cycloalkyl (meth)acrylates, such as cyclohexyl (meth)acrylate, phenyl-ethyl (meth)acrylate, phenylpropyl (meth)acrylate, and acrylates of heterocyclic alcohols such as furfuryl (meth)acrylate.

Other said further monomers which are suitable are for example (meth)acrylamide and derivatives thereof which are substituted by $C_1$-$C_4$alkyl on the nitrogen atom.

Other significant monomers are hydroxy-functional monomers, e.g., $C_1$-$C_{15}$-alkyl (meth)acrylates substituted by one or two hydroxy groups. Particularly significant hydroxy-functional comonomers are $C_2$-$C_8$-hydroxyalkyl (meth)acrylates, such as n-hydroxyethyl, n-hydroxypropyl, or n-hydroxybutyl (meth)acrylate.

The co-use of comonomers containing salt-forming groups is particularly recommendable for the preparation of auto-dispersible copolymers suitable, for example, for aqueous secondary dispersions. Monomers having salt-forming groups are, in particular, itaconic acid, acrylic acid, and methacrylic acid.

The percentage of said further comonomers in the copolymer can be from 0 to 50 wt %, preferably from 0 to 20 wt % and more preferably from 0 to 10 wt %.

The preparation of the copolymer A) takes place by free-radical polymerization. Suitable methods of polymerization, such as polymerization in substance, solution, suspension, or emulsion, are known to the person skilled in the art.

In the case of solution polymerization, there is obtained a solution of the copolymer in an organic solvent.

Preferably the copolymer is prepared by solution polymerization followed by dispersion in water or, more preferably, by emulsion polymerization, so that aqueouscopolymer dispersions are formed.

The emulsion polymerization can be carried out batchwise, with or without the addition of seed latices, by a method involving the use of a starting batch of all, some, or one of the individual constituents of the reaction mixture, or preferably by a method using a starting batch containing some of the components and subsequently metering in the remaining constituents of the reaction mixture individually or together, or by a metering technique not using any starting batch in the reactor.

When using the emulsion polymerization method, the comonomers can be polymerized in the usual manner in the presence of a water-soluble initiator and an emulsifier at preferably from 30° to 95° C.

Suitable initiators are, e.g., sodium, potassium, and ammonium persulfate, tert-butyl hydroperoxides, water-soluble azo compounds or alternatively redox initiators such as $H_2O_2$/ascorbic acid.

The emulsifiers used are, e.g., alkali metal salts of longer-chain fatty acids, alkyl sulfates, alkyl sulfonates, alkylated aryl sulfonates or alkylated diphenyl ether sulfonates. Other suitable emulsifiers are reaction products of alkylene oxides, in particular ethylene oxide or propylene oxide with fatty alcohols, fatty acids, or phenol, or alkylphenols.

In the case of aqueous secondary dispersions the copolymer is first of all prepared by solution polymerization in an organic solvent and is subsequently dispersed in water, with the addition of salt-forming substances, e.g., ammonia, to copolymers containing carboxylic acid groups, such dispersion being effected without the use of an emulsifier or dispersing aid. The organic solvent can be removed by distillation. The preparation of aqueous secondary dispersions is known to the person skilled in the art and described in, e.g., D-A 3,720,860.

In order to regulate the molecular weight, modifiers can be used during polymerization. Suitable modifiers are, e.g., SH-containing compounds such as mercaptoethanol, mercaptopropanol, thiophenol, thioglycerol, ethyl thioglycolate, methyl thioglycolate, and tert-dodecyl mercaptan.

The type and amount of the comonomers are expediently such that the copolymer obtained has a glass transition temperature preferably between −60° C. and +140° C. and more preferably between −30° and +80° C. and most preferably, particularly when the copolymer is to be used as art adhesive, between −30° and +20° C. The glass transition temperature of the copolymer can be determined by usual methods such as differential thermoanalysis or differential scanning calorimetry (cf, e.g., ASTM A341 8/82, "midpoint temperature") bestimmen.

When the copolymer is not self-cross-linking, ie contains no monomers c), a suitable cross-linking agent can be added to the copolymer to effect cross-linking. The cross-linking agent is usually a compound which contains at least two keto or aldehyde groups, or at least one keto group and one aldehyde group.

Such compounds are, e.g., succindialdehyde, glutardialdehyde, and terephthaldialdehyde.

Other suitable cross-linking agents are, in particular, free-radical copolymers—also referred to below as polymeric cross-linking agents—which contain the aforementioned monomers c) in the form of polymerized units.

Examples of suitable polymeric cross-linking agents are those composed of from 30 to 99.9 wt %, preferably from 70 to 99.9 wt %, of monomers b), from 0.1 to 30 wt %, preferably from 0.1 to 10 wt %, of monomers c), and from 0 to 50 wt %, preferably from 0 to 20 wt %, of monomers d). Concerning the nature of the monomers, their glass transition temperature, and their preparation preferably the same applies as stated above concerning the copolymers.

Furthermore, the copolymers of the invention can cross-link compounds containing hydroxyl groups, in particular hydroxyl group-containing copolymers.

The cross-linking agent, if required, is preferably added to the solution or dispersion of the copolymers.

Alternatively, the copolymer and the cross-linking agent are brought together only when required for use, e.g., for coating surfaces. To this end the cross-linking agent could, for example, be first of all applied to the surface as a primer, after which a coating of the dispersion or solution of copolymer would be applied.

The solution or dispersion of the copolymers of the invention is suitable inter alia for use as paints and coating compositions, e.g., for plastics, wood, or metal surfaces, surfaces of mineral building materials such as concrete or clay, road surfaces containing asphalt or bitumen or for textiles, non-woven fabrics, leather, and paper. They are equally suitable for use in the field of building chemicals, e.g., as adhesives, sealing compounds, binding agents or the like.

The dispersions or solutions can, depending on their intended use, further contain usual auxiliaries and additives. These include, for example, fillers such as quartz powder, quartz sand, microdispersed silicic acid, heavy spar, calcium carbonate, chalk, dolomite, and talcum, which are often used together with suitable wetting agents such as polyphosphates, e.g., sodium hexamethaphosphate, naphthalenesulfonic acid, ammonium or sodium polyacrylates, the wetting agents generally being added in a concentration of from 0.2 to 0.6 wt %, based on the filler.

In addition, fungicides can be added to effect preservation. These are generally used in amounts of from 0.02 to 1 wt %, based on the dispersions or solutions. Suitable fungicides are, for example, phenol or cresol derivatives or tin-organic compounds.

The dispersions or solutions are also particularly suitable for use as sealing or adhesive formulations, in particular as laminating adhesives for the preparation of laminated films and high-gloss sheets. As such, they can contain, in addition to the aforementioned additives, other special auxiliaries and additives as are usual in adhesive technology. These include, for example, thickeners, plasticizers or even tackifying resins such as natural resins or modified resins, e.g., colophonium esters or synthetic resins such as phthalate resins.

The dispersions or solutions of the self-cross-linking or non-self-cross-linking copolymers additionally containing a cross-linking agent are stable in storage. Cross-linking occurs at room temperature with volatilization of the solvent or dispersing agent. The cross-linking properties and the good adhesion properties of the copolymers are not impaired by the presence of metal salts.

The coatings or adhesive joints obtained when using these dispersions or solutions show good resistance to chemicals or solvents; and good internal strength (cohesion).

In the experiments described below demineralized water is used and the percentages are by weight, unless otherwise stated.

EXAMPLES

The precursors of the general formulas III and IV are first synthesized, from which the hydroxylamine derivatives of the inventionen are then prepared.

EXAMPLE 1

O-(2-acroyloxypropyl)hydroxylammonium chloride, referred to below as Monomer $a_1$, of the formula

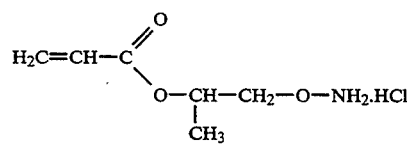

Precursor IV
in which $R^1$ denotes H, A denotes

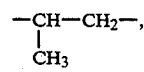

$R^2$ denotes —$CH_3$ and
$R^3$ denotes —$OC_2H_5$.

To a mixture of 30 mL of diethyl ether, 32.2 g (0.20 mol) of ethyl O-(2-hydroxypropyl)acetohydroxamate, 24.2 g (0.24 mol) of triethylamine, and 0.10 g of 2,6-di-tert-butyl-p-cresol (stabilizer) there are added dropwise at 10° C. (cooling with ice) a solution of 120 mL of diethyl ether and 22.4 g (0.24 mol) of acrylic chloride over a period of 30 min. The reaction mixture is allowed to react to completion over a period of 5 h at room temperature and it is then shaken with a solution of 33.1 g (0.24 mol) of potassium carbonate in 100 g of water. Following separation of the aqueous phase the ethereal solution is evaporated down under water-jet vacuum at room temperature and the residue is distilled following evaporation under oil pump vacuum. There are obtained 32.5 g (76%) of ethyl O-(2-acroyloxypropyl)acetohydroxamate, bp 66°–68° C./0.1 mbar.

1.2 Monomer $a_1$

To a mixture of 114 mL of dioxane, 45.4 g (0.225 mol HCl) of an 18.1% strength solution of HCl in dioxane and 4.10 g (0.228 mol) of water there are added dropwise, at room temperature over a period of 15 min, 24.5 g (0.114 mol) of the end product obtained under 1.1. The mixture is allowed to react over a period of 3 h at room temperature. 570 mL of diethyl ether are then added dropwise and following a crystallization time of 20 h there are isolated, by filtration, 19.2 g of product, mp 92°–94° C. (recrystallized from ethanol/diethyl ether). The yield is 93% of theory.

| Elementary analysis | C | H | O | N | Cl |
|---|---|---|---|---|---|
| calculated | 39.68 | 6.66 | 26.43 | 7.71 | 19.52 |
| found | 39.25 | 6.82 | 26.63 | 7.62 | 19.81 |

EXAMPLE 2

O-(2-methacroylamidocarbonyloxyethyl)-hydroxylammonium chloride, referred to below as Monomer $a_2$, of the formula

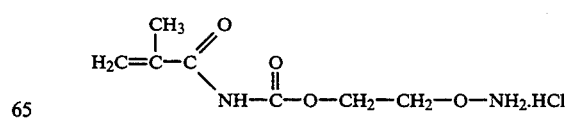

2.1 Precursor III
in which Z denotes

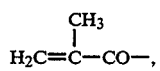

A denotes —CH$_2$—CH$_2$—,
R$^2$ denotes —CH$_3$, and R$^3$ denotes —OC$_2$H$_5$.

To a mixture of 29.4 g (0.20 mol) of ethyl o-(2-hydroxyethyl)acetohydroxamate, 40 mL of dichloromethane and 0.1 g of 2,6-di-tert-butyl-p-cresol (stabilizer) there is added dropwise, at from 20° to 22° C., a solution of 22.2 g (0.20 mol) of methacroyl isocyanate in 25 mL of dichloromethane and the reaction is allowed to go to completion over a period of 1 h at room temperature. The solvent is evaporated off at 30° C. in vacuo and the residue obtained after evaporation (51.5 g, 100% crude yield) is recrystallized from 200 mL of methyl-tert-butyl ether at −25° C. The pure product is isolated by filtration and melts at 66°–68° C.

| Elementary analysis | C | H | O | N | |
|---|---|---|---|---|---|
| Formula | 11 | 18 | 5 | 2 | |
| Theory | 51.16 | 7.03 | 30.97 | 10.85 | Mol. Wt. = 258,3 |
| Found | 51.1 | 7.0 | 31.0 | 10.6 | |
| Atomic ratio | 5.62 | 9.18 | 2.56 | 1.00 | |

2.2 Monomer a$_2$

A mixture of 30 g water, 15.0 g (0.15 mol) of conc. Hydrochloric acid and 19.4 g (0.075 mol) of the end product obtained under 2.1 is stirred for 3 h at room temperature. The solution is evaporated down at room temperature in vacuo (0.5 mbar) and the distillation residues are dissolved in 20 mL of ethanol. Following the addition of 200 mL of diethyl ether crystallization is allowed to proceed over a period of 20 h at 5° C. There are isolated, by filtration, 16.2 g (96 % of theory) of product mp 188° C.

EXAMPLE 3

O-(2-methacroyloxypropyl)hydroxylammonium chloride, referred to below as Monomer a$_3$, of the formula

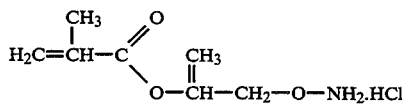

3.1 Precursor IV
in which R$^1$ denotes —CH$_3$, A denotes

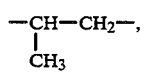

R$^2$ denotes —CH$_3$ and
R$^3$ denotes —OC$_2$H$_5$.

To a mixture of 95 g (0.59 mol) of ethyl O-(2-hydroxypropyl)acetohydroxamate, 60.2 g (0.59 mol) of triethylamine and 0.1 g of phenothiazine (stabilizer) there are added dropwise, at 80° C. 110 g (0.71 mol) of methacrylic anhydride. Following a reaction time of 10 h at 80° C., the reaction mixture is cooled to 20° C. and stirred with a solution of 98.5 g (0.71 mol) of potassium carbonate in 500 mL water for 45 min. The separated organic phase yields, on distillation in vacuo, ethyl O-(2-methacroyloxypropyl)acetohydroxamate, bp 65°–67° C./0.1 mbar.

3.2 Monomer a$_3$

The hydrolysis of the precursor IV obtained under 3.1 with hydrochloric acid is effected as in the preparation of monomer a$_1$ in dioxin acting as solvent and yields O-(2-methycroyloxypropyl)hydroxylammonium chloride having a mp of 75°–77° C.

| Elementary analysis | C | H | N | Cl |
|---|---|---|---|---|
| Calculated | 42.97 | 7.21 | 7.16 | 18.12 |
| Found | 42.65 | 7.50 | 7.12 | 18.03 |

EXAMPLE 4

O-(2-methacroyloxyethyl)hydroxylammonium chloride, referred to below as Monomer a$_4$, of the formula

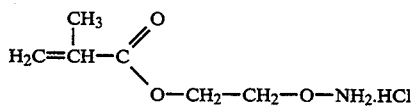

4.1 Precursor IV
in which
R$^1$ denotes —CH$_3$,
A denotes —CH$_2$—CH$_2$—,
R$^2$ denotes —CH$_3$, and R$^3$ denotes —CO$_2$H$_5$.

To preparation of ethyl O-(2-methacroyloxyethyl)acetohydroxamate from ethyl O-(2-hydroxyethyl)acetohydroxamate and methacrylic anhydride is effected in the same manner as precursor 3.1 except that the reaction temperature is 64° C. Bp 65° C./0.1 mbar.

| Elementary analysis | C | H | O | N | |
|---|---|---|---|---|---|
| Formula | 10 | 17 | 4 | 1 | |
| Theory | 55.80 | 7.96 | 29.73 | 6.51 | Mol. Wt. = 215.2 |
| Found | 55.8 | 8.1 | 29.4 | 6.9 | |
| Atomic ratio | 9.43 | 16.31 | 3.73 | 1.00 | |

4.2 Monomer a$_4$

The hydrolysis of the precursor of 4.1 is carried out in accordance with the directions given under 2.2 (Monomer a$_2$) and yields O-(2-methacroyloxyethyl)hydroxylammonium chloride having an mp of 84°–86° C.

Preparation Of The Dispersions

The polymerizations are carried out in conventional boilers with stirring.

Dispersion Type 1

A mixture of 250 g of water, 40 g of a 15 wt % strength aqueous solution of sodium lauryl sulfate, 15 g of a 40 wt % strength aqueous solution of nonylphenol ethoxylized with 50 mol of ethylene oxide, 21.3 g of feed 1 and 10.1 g of feed 2 is placed in the reactor and heated with stirring to 75° C. Following the prepolymerization, the residual feed 1 is fed to the polymerization mixture at a constant rate.

On completion of feed 1 there are added 6 g of a 25 wt % strength aqueous ammonia solution. Feed 3 is then metered in at a constant rate over a period of 55 minutes. Feed 2 is metered in at a constant rate over a period of 2.5 hours starting at the same time as the commencement of the residual feed 1. Polymerization is then allowed to continue for a further hour at constant temperature and the mixture is then cooled and filtered.

| Feed 1 (stirred): | |
|---|---|
| 108.3 g | water |
| 7.5 g | 40 wt % strength solution of nonylphenol ethoxylated with 50 mol of ethylene oxide |
| 300 g | n-butyl acrylate |
| 30 g | methyl methacrylate |
| 9 g | acrylic acid |
| 3 g | 50 wt % strength aqueous solution of acrylamide |
| Feed 2: | |
| 100 g | water |
| 0.6 g | sodium peroxodisulate |
| Feed 3 (stirred): | |
| 74.3 g | water |
| 40 g | 15 wt % strength aqueous solution of sodium lauryl sulfate |
| 7.5 g | 40 wt % strength aqueous solution of nonylphenol ethoxylated with 50 mol of ethylene oxide |
| 24 g | n-butyl acrylate |
| 222 g | methyl methacrylate |
| 12 g | monomer a) |
| 3 g | 50 wt % strength aqueous solution of acrylamide. |

In this way the dispersions D1 to D4 (cf table) are prepared.

Dispersion Type 2

The procedure is the same as for Dispersion Type 1.

| Feed 1; | as for D1 |
|---|---|
| Feed 2; | as for D1 |
| Feed 3 (stirred): | |
| 50.3 g | water |
| 40 g | 15 wt % strength solution of sodium lauryl sulfate |
| 7.5 g | 40 wt % strength aqueous solution of nonylphenol ethoxylated with 50 mol of ethylene oxide |
| 24 g | n-butyl acrylate |
| 222 g | methyl methacrylate |
| 6 g | monomer a) |
| 30 g | 20 wt % strength aqueous solution diacetone acrylamide |
| 3 g | 50 wt % strength aqueous solution of acrylamide. |

In this way, the dispersions D5 to D8 are prepared.

Auxiliary dispersion AD 200 g of water, 37 g of feed 1 and 20 g of feed 2 are placed in the reaction vessel and heated to 85° C. After 15 minutes, feed 1 is added at a steady rate over a period of 2 h, and feed 2 is added at a steady rate over a period of 2.5 h. Following the latter addition of initiator (feed 2), the dispersion is stirred for a further hour at 85° C.

| Feed 1; (this feed is stirred during polymerization) | |
|---|---|
| 107.5 g | water |
| 400 g | ethyl acrylate |
| 90 g | methyl methacrylate |
| 50 g | 20 wt % strength aqueous diacetone acrylamide solution |
| 50 g | 20 wt % strength solution of sodium lauryl sulfate |
| 50 g | 20 wt % strength solution of the reaction product of p-phenol, isophenol, or nonylphenol with ca 50 mol of ethylene oxide in water |
| Feed 2; | |
| 100 g | water |
| 3 g | sodium persulfate |

Technological tests

Cross-linkability (tested by observing the degree of swell and determining the extractable portions)

In each test, 10 g of the dispersions or dispersion mixtures listed in the table below are converted to film and the film are dried for 1 week at room temperature. The swelling behavior of these films in tetrahydrofuran, as a measure of the degree of cross-linking, is then examined by leaving ca 1 g of the film specimens in tetrahydrofuran for 24 h and measuring the solvent uptake in %.

Crosslinked polymers swell due to the absorption of solvent. As the degree of cross-linking increases less swelling occurs, since less solvent can be absorbed by the more closely crosslinked polymer. Uncross-linked or hardly crosslinked polymers are dissolved by solvents to a great extent or swell excessively when a small number of cross-linking sites is present.

The extractable portions are determined by reweighing at room temperature after drying in a drying cabinet at 80° C. over a period of 4 h.

The results are listed in the table.

Adhesive properties for laminations with high-gloss sheet material

The dispersions or dispersion mixtures listed in the table are knife-coated onto cardboard specimens printed with offset inks, the dry thickness of the resulting coatings being 5 g/m². after ca 30 s the coated board is laminated with biaxially orientated polypropylene sheets or acetate sheeting.

Following 6 weeks' storage at room temperature, the boards are tester to observe whether the process of tearing off the sheet material causes ink to become detached from the cardboard and whether, in groove areas (caused by embossments in the cardboard), the sheet material has become detached from, or is only loosely attached to, the board (groove stability).

All of the compositions and results are summarized in the following table.

TABLE

| Ex. No. | Dispersion No. | Added dispersion | Monomer a) | Swell [%] | Extraction [%] | Tests on high-gloss sheet material[2]) |
|---|---|---|---|---|---|---|
| 1 | 1 | — | $a_1$ | 2900 | 20 | + |
| 2 | 2 | — | $a_2$ | 2710 | 18 | + |
| 3 | 3 | — | $a_3$ | 2850 | 18 | + |
| 4 | 4 | — | $a_4$ | 3010 | 21 | + |
| 5 | 1 | AD[1]) | $a_1$ | 1310 | 5 | ++ |
| 6 | 2 | AD[1]) | $a_2$ | 1750 | 11 | ++ |
| 7 | 3 | AD[1]) | $a_3$ | 1890 | 15 | ++ |
| 8 | 4 | AD[1]) | $a_4$ | 1910 | 16 | ++ |
| 9 | 5 | — | $a_1$ | 1220 | 3 | ++ |
| 10 | 6 | — | $a_2$ | 1410 | 4 | ++ |
| 11 | 7 | — | $a_3$ | 1340 | 10 | ++ |
| 12 | 8 | — | $a_4$ | 1480 | 9 | ++ |
| Comp.: | AD | — | — | dissolved | dissolved | no adhesion |

[1])mixture of the dispersions in a ratio by weight of 1:1.
[2])++; very good groove stability, ink detachment from the cardboard
+; good groove stability, slight ink detachment from the cardboard

We claim:

1. A hydroxylamine derivative of the general formula

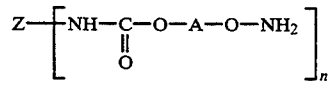

I or

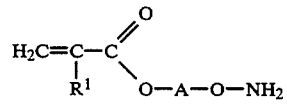

II in which A denotes a divalent connecting link, $R^1$ can be a hydrogen atom or a $C_1$–$C_4$alkyl group, Z stands for an n-valent organic radical, which contains a copolymerizable ethylenically unsaturated group, and n is an integer from 1 to 3, and their salts.

* * * * *